United States Patent [19]
Yoshida et al.

[11] Patent Number: 5,276,177
[45] Date of Patent: Jan. 4, 1994

[54] PHYSIOLOGICALLY ACTIVE SUBSTANCE

[75] Inventors: Mayumi Yoshida, Sagamihara; Yutaka Saito, Machida; Tetsuya Matsuno, 2-19-24, Naka, Kunitachi-shi, Tokyo, all of Japan

[73] Assignees: Tetsuya Matsuno; MPI Limited, a Japanese Corp., both of Tokyo, Japan

[21] Appl. No.: 899,730

[22] Filed: Jun. 17, 1992

[30] Foreign Application Priority Data

Aug. 29, 1991 [JP] Japan .................................. 3-219021

[51] Int. Cl.$^5$ .............................................. C07C 61/12
[52] U.S. Cl. ..................................................... 562/501
[58] Field of Search ........................... 562/501; 514/553

[56] References Cited

U.S. PATENT DOCUMENTS 5,008,441  4/1991  Nakanishi .............................. 560/75

OTHER PUBLICATIONS

G. Morales et al., "Diterpenoids and Flavonoids from *Baccharis boliviensis*," Chem. Abstr. 1991, 114, 39206u.
S. Scheller et al., "Antitumoral Property of Ethanolic Extract Propolis in Mice Bearing Ehrlich Carcinoma, Compared to Bleomycin," Z. Naturforsch, C, 1989, 44, 1063-1065.
F. Bohlmann et al., "Thirteen Kolavane Derivatives from Symphyopappus Species," Phytochemistry, 1981, 20, 1657-1663.
C. Zdero et al., "Ent–Clerodanes and Other Constituents from Bolivian Baccharis Species," Phytochemistry, 1989, 28, 531-542.
M. Toyota et al., "Clerodane, Laurane and Labdane Diterpenoids from the Liverwort *Jungermannia Infusca*," Phytochemistry, 1989, 28, 3415-3419.
M. Toyota et al., "Clerodane-type Diterpenic Acid from the Liverwort *Jungermannia Infusca*," Phytochemistry, 1989, 28, 2507-2509.

*Primary Examiner*—Michael L. Shippen
*Attorney, Agent, or Firm*—Kazuyuki Yamazaki

[57] ABSTRACT

A novel physiologically active substance is represented by the formula.

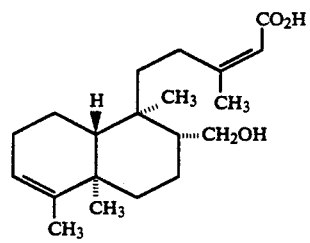

The substance is preferably derived from propolis, has excellent antitumor activity and is useful as an antitumor drug.

1 Claim, No Drawings

PHYSIOLOGICALLY ACTIVE SUBSTANCE

BACKGROUND OF THE INVENTION

1. Field of the Invention

The present invention relates to a novel physiologically active substance. A novel physiologically active substance is preferably derived from propolis, has excellent antitumor activity and is useful as an antitumor drug.

2. Prior Art

Propolis is a kind of glue in which resins collected by honeybees are mixed with saliva secretion, beewax, pollen, etc., and known as a folk medicine having a variety of pharmacological activities including antimicrobial activity and anti-inflammatory activity.

It is known that an ethanol extract of propolis has antitumor activity [Z. Naturforsch, C 44. 1063, (1989)].

Further, it is known that phenetyl cafeate, one component of propolis, represented by the formula (II),

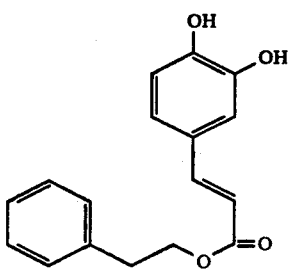

has antitumor activity [Experientia 44, 230, (1988)].

The process for preparing a propolis extract having antitumor activity has been disclosed by the present inventors (JP,A Hei 3-162596).

Further, as a compound having a skeleton similar to that of the compound of the present invention, compounds represented by the following formulae are known.

Bolivianol represented by the formula (III) [Bol. Soc. Chil, Quim., 35, 257, (1990) (Chemical Abstract 114, 39206u)].

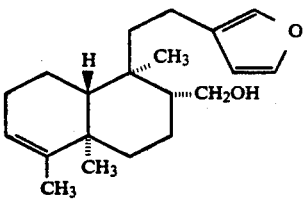

A compound represented by the formula (IV),

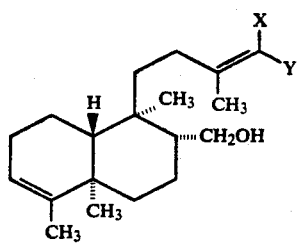

(wherein each of X and Y represents $CH_2OH$ or each of X and Y, independently of other, represents $CH_2OH$ or H) [Phytochemistry 28, 531, 3415 (1989)].

A compound represented by the formula (V),

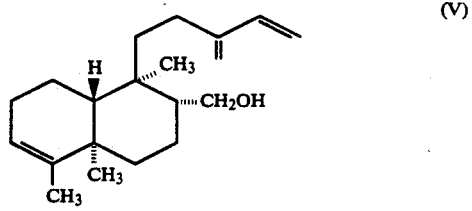

[Phytochemistry 28, 3415, 2507 (1989)].

A compound represented by the formula (VI),

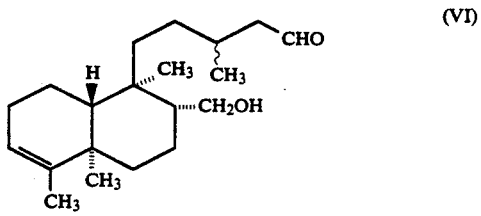

[Phytochemistry 20, 1657 (1981)].

However, there is no report on the antitumor activity of these compounds.

SUMMARY OF THE INVENTION

It is an object of the present invention to provide a compound having excellent antitumor activity.

The present inventors have found that a substance having antitumor activity is present in propolis. This substance has been isolated and purified, and its physical and chemical properties have been studied. As a result, it has been found to be a novel substance, and named a novel physiologically active substance.

According to the present invention, there is provided a novel physiologically active substance represented by the formula (I).

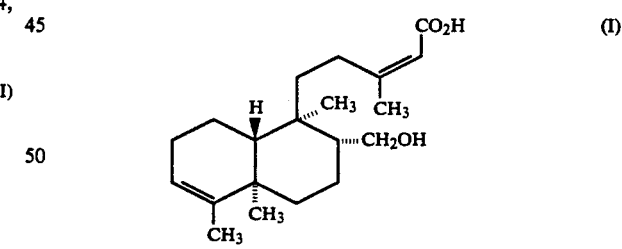

DETAILED DESCRIPTION OF THE INVENTION

The present invention will be detailed hereinafter.

The physical and chemical properties of the novel physiologically active substance are as follows.

(i) Molecular weight: 320

(ii) Molecular formula: $C_{20}H_{32}O_3$ (iii) Mass spectrometry: SIMS method (using glycerol as a matrix): m/z 321 $(M+H)^+$ High-resolution SIMS spectrum: 321.2403

Calculated as $C_{20}H_{33}O_3$: 321.2430

(iv) Specific rotatory power: $[\alpha]_D^{25} = -83°$ (c=0.44, methanol)

(v) Ultraviolet absorption spectrum: (in methanol) λmax: 212 nm (ε=4,600, 288 nm (ε=2,600)

(vi) Infrared absorption spectrum: (KBr tablet method) ν(cm$^{-1}$): 3,600–2,400, 3,450, 2,941, 1,695, 1,641, 1,439, 1,385, 1,259

(vii) $^1$H-NMR: (500 MHz, CD$_3$OD) internal standard TMS, δ (ppm): 5.63 (1H, br, s), 5.18 (1H, m), 3.84 (1H, dd, J=10.6, 3.1 Hz), 3.21 (1H, br, t), 1.89 (3H, d, J=1.3 Hz), 1.58 (3H, d, J=1.3 Hz), 1.03 (3H, s), 0.75 (3H, s)

(viii) $^{13}$C-NMR: (125 MHz, CD$_3$OD) internal standard TMS, δ (ppm): 170.4, 161.7, 145.1, 121.8, 117.7, 64.4, 47.9, 45.5, 39.4, 39.2, 37.7, 37.6, 28.4, 27.7, 25.4, 23.2, 20.3, 19.5, 18.8, 18.2

(ix) Solubility: Soluble in methanol, ethyl acetate, chloroform and DMSO. Sparingly soluble in acidic water.

(x) Color reaction: Positive to an iodine reagent, a BCG reagent and a cerium sulfate reagent.

(xi) Appearance: Colorless solid (xii) High performance liquid chromatography: Reversed phase silica gel filler column: YMC Co. AM-312 (ODS, spherical, 5 μm, pore diameter 60 angstrom, 6.0 mmφ×150 mm); eluent: 0.02M acetic acid-ammonium acetate (pH 5.0)-methanol [25:75 (v/v)]; flow rate 1 ml/min; detection: detected by means of 240 nm ultraviolet absorption; retention time: 16.7 minutes The biological activity of the novel physiologically active substance will be explained hereinafter.

Growth inhibition to Hela S3 cells 0.1 Milliliter of a test compound properly diluted with an MEM culture containing 10% fetal bovine serum and 2 mM of glutamine was placed in each of 96 wells of a microtiter plate. Then, trypsinized HeLa S3 cells (ATCC HTB22) were adjusted with the above culture to form a solution containing 3×10$^4$ cells/ml, and 0.05 ml of the solution was added to each well.

The above plate was cultured in a carbonic acid gas incubator at 37° C. for 72 hours, and then culture supernatants were removed. 0.1 Milliliter of a culture medium containing 0.02% Neutral Red was added to each well, and the plate was cultured in the carbonic acid gas incubator at 37° C. for 1 hour to stain the cells. After culture supernatants were removed, the remainders were once washed with a physiological saline solution. Then, the dyestuff was extracted with 0.001N hydrochloric acid/30% ethanol, and the absorbance at 550 nm was measured with a microplate reader. In comparison between the absorbance of untreated cells and the absorbance of cells treated with the known concentration of the test compound, the growth inhibition ratio of the cells was calculated on the basis of the following equation.

$$\text{Growth inhibition ratio (\%)} = \frac{A - B}{C - B} \times 100$$

A: Absorbance of cells treated with the compound
B: Absorbance of a well containing no cells
C: Absorbance of untreated cells On the basis of the above-obtained growth inhibition ratio, the test compound concentration at which the growth of cells was 50% inhibited (IC$_{50}$) was calculated. Table 1 shows the result.

TABLE 1

| Test compound | IC$_{50}$ (μg/ml) |
| --- | --- |
| Novel physiologically active substance | 87.0 |

TABLE 1-continued

| Test compound | IC$_{50}$ (μg/ml) |
| --- | --- |
| derived from propolis | |

The cell cycle was analyzed with a flow cytometer to show that the test compound terminated the growing cells at S phase and destroyed them.

As described above, the novel physiologically active substance exhibits antitumor activity against cultured tumor cells and is useful as an antitumor drug.

When the novel physiologically active substance is used as an antitumor drug, it is administered in a dose of 20 to 500 mg/kg-body/day, preferably 60 to 100 mg/kg-body/day. The novel physiologically active substance is dissolved in a pharmaceutically acceptable solvent such as alcohols (e.g., ethanol) and DMSO (dimethylsulfoxide), and the resultant solution is administered intravenously or orally.

The process for the preparation of the novel physiologically active substance will be described hereinafter.

One embodiment of the process for the preparation of an extract containing the compound of the present invention will be described in Referential Example. The novel physiologically active substance is isolated from the extract and purified according to a generally used method, e.g., a high performance liquid chromatography. The characteristic properties of the novel physiologically active substance during the purification step can be traced by ultraviolet absorption.

Examples of the present invention will be described hereinafter. In addition, the physicochemical data of the novel physiologically active substance was measured by the following apparatus.

Mass spectrum: M-80B mass spectrometer supplied by Hitachi Ltd. SX-102 mass spectrometer supplied by JEOL LTD.

Optical rotation: DIP-370 spectrometer supplied by Nippon Bunko K. K.

Ultraviolet absorption spectrum: UV-2200 spectrophotometer supplied by Shimadzu Corp.

Infrared absorption spectrum: JIR-RFX3001 infrared spectrophotometer supplied by JEOL LTD.

NMR spectrum: AM500 nuclear magnetic resonance apparatus supplied by Bulker Co., Ltd.

EXAMPLE 1

2 Milligrams of the fraction obtained by the use of acidic acetonitrile in Referential Example was dissolved in methanol, and purified with an ODS column [YMC SH345-5, supplied by YMC Co.] for high performance liquid chromatography [Elution conditions: 75% (V/V) methyl alcohol-20 mM ammonium acetate, pH 5.0, flow rate 10 ml/minute]. In a retention time of 49 to 51 minutes, a fraction absorbing ultraviolet light (wavelength 240 nm) was obtained. The above procedures were repeated, and the methyl alcohol was removed from the resultant fraction under reduced pressure. 1N hydrochloric acid in an amount of 1/10 by volume was added to the aqueous solution, and the solution was subjected to extraction with ethyl acetate. An organic layer was washed with saturated sodium chloride aqueous solution according to a conventional method, and dried over anhydrous sodium sulfate. The organic solvent was distilled off under reduced pressure to give 4.4 mg of a novel physiologically active substance as a colorless solid.

The physical and chemical properties and primary structure of the novel physiologically active substance were as described previously.

EXAMPLE 2

The fraction obtained by the use of ethyl alcohol in Referential Example was treated in the same manner as in Example 1 to give a novel physiologically active substance of the present invention.

REFERENTIAL EXAMPLE

100 Grams of propolis of Brazilian origin was mixed with 10-fold (V/V) 99.5% (W/W) ethyl alcohol, and the mixture was stirred at room temperature. The resultant suspension was filtered through a filter paper sheet under reduced pressure to give an ethyl alcohol extract solution of propolis. Then, the solvent in the so-obtained ethyl alcohol extract solution was distilled off under reduced pressure, and 30 g of the resultant residue was dissolved in a water/ethyl acetate mixed solution having a mixing ratio of 1:1 to obtain an ethyl acetate extract solution of propolis as an organic layer. The solvent of the so-obtained extract was distilled off under reduced pressure, and 20 g of the resultant residue was dissolved in 99.5% (W/W) methyl alcohol, and insolubles were centrifugally removed to give a methyl alcohol extract solution. The so-obtained methyl alcohol extract solution was purified with an ODS type column (TOSOH ODS 80 TM, supplied by TOSOH CORP.) for high performance liquid chromatography brought into an equilibrium with 70% (V/V) acidic methyl alcohol (adjusted to pH 3.5 with acetic acid) [Elution conditions: acetonitrile 70 to 100% (V/V), pH 3.5]. Thereafter, fractions having an acidic methyl alcohol concentration of 82 to 88% (V/V) were collected. The so-obtained fractions were put together, and the solvent was distilled off under reduced pressure to give 200 mg of a residue. The so-obtained residue was dissolved in 70% (V/V) acidic acetonitrile (adjusted to pH 3.5 with acetic acid), and the resultant solution was purified with an ODS type column (TOSOH ODS 80TM, supplied by TOSOH CORP.) for high performance liquid chromatography brought into an equilibrium with 70% (V/V) acidic acetonitrile (adjusted to pH 3.5 with acetic acid) [Elution conditions: acetonitrile 70 to 100% (V/V), pH 3.5]. Thereafter, fractions having an acetonitrile concentration of 73 to 76% were collected. The so-obtained fractions were put together, and the solvent was distilled off under reduced pressure to give 50 mg of a residue. Then, the so-obtained residue was dissolved in 70% (V/V) acetonitrile, and the resultant solution was purified with an ODS type column (TOSOH ODS 80TM, supplied by TOSOH CORP.) for high performance liquid chromatography brought into an equilibrium with 75% (V/V) ethyl alcohol [Elution conditions: ethyl alcohol 75 to 90% (V/V)]. Then, fractions having an ethyl alcohol concentration of 80 to 85% were collected. A propolis extract was obtained by collecting posterior fractions from main fractions absorbing ultraviolet light (wavelength 254 nm).

According to the present invention, there is provided a novel physiologically active substance which has antitumor activity.

What is claimed is:

1. A compound represented by the formula (I):

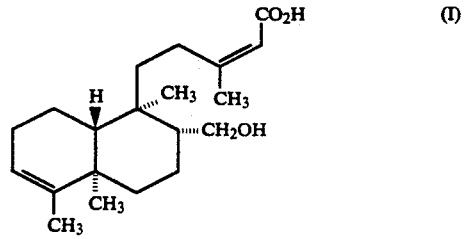

and characterized by the following physical and chemical properties:

(a) Specific rotatory power: $D^{25} = -83°$ (c=0.44, methanol)

(b) Ultraviolet absorption spectrum: (in methanol) λmax: 212 nm ($\epsilon=4,600$, 288 nm) ($\epsilon=2,600$)

(c) Infrared absorption spectrum: (KBr tablet method) $\nu(cm^{-1})$: 3,600–2,400, 3,450, 2,941, 1,695, 1,641, 1,439, 1,385, 1,259

(d) Solubility: Soluble in methanol, ethyl acetate, chloroform and DMSO. Sparingly soluble in acidic water (e) Color reaction: Positive to an iodine reagent, a BCG reagent and a cerium sulfate reagent (f) High performance liquid chromatography: Reversed phase silica gel filler column: (ODS, spherical, 5 μm, pore diameter 60 angstrom, 6.0 mmφ×150 mm); eluent: 0.02M acetic acid-ammonium acetate (pH 5.0)-methanol; flow rate 1 ml/min; detection: detected by means of 240 nm ultraviolet absorption; retention time; 16.7 minutes.

* * * * *